United States Patent [19]
Janghorbani et al.

[11] Patent Number: 6,006,754
[45] Date of Patent: Dec. 28, 1999

[54] METHOD FOR MEASURING FAT DIGESTION AND ABSORPTION FORMULATION TO AID IN MEASURING FAT ABSORPTION

[75] Inventors: Morteza X. Janghorbani, Chicago, Ill.; Sally A. Schuette, Crown Point, Ind.; Mitchell B. Cohen, Cincinnati, Ohio

[73] Assignee: Biochem Analysis Corporation, Chicago, Ill.

[21] Appl. No.: 09/005,305

[22] Filed: Jan. 9, 1998

[51] Int. Cl.$^6$ .................................................. A61B 19/00
[52] U.S. Cl. ........................ 128/898; 424/94.21; 424/690
[58] Field of Search ........................... 424/690, 1, 94.21; 436/86

[56] References Cited

U.S. PATENT DOCUMENTS

| | | | |
|---|---|---|---|
| 4,826,679 | 5/1989 | Roy | 424/94.21 |
| 4,840,795 | 6/1989 | Ben-Sasson | 424/690 |

OTHER PUBLICATIONS

Schuette et al. Journal of the American College of Nutrition, vol. 12, No. 3, pp. 307–315 (1993) "Dysprosium as a Non–absorbable Marker for Studies of Mineral Absorption with Stable Isotope Tracers in Human Subjects".

*Primary Examiner*—Max Hindenburg
*Assistant Examiner*—Brian Szmal
*Attorney, Agent, or Firm*—Cherskov & Flaynik

[57] ABSTRACT

A method for measuring fat assimilation, such as fat digestion and fat absorption, in a person is provided comprising feeding the person labeled fat, nonabsorbable marker, and a means for coloring stool; allowing the fat, marker and stool coloring means to travel through the digestive tract of the person; monitoring stool from the person for the appearance of the coloring means; collecting stool containing the coloring means; and measuring the amount of marker and labeled fat in the stool to determine the portion of fat digested and/or absorbed by the system. Also provided is a formulation to facilitate one-step administration and specimen collection of a fat-digestion and fat-absorption determinant.

19 Claims, 2 Drawing Sheets

US 6,006,754

METHOD FOR MEASURING FAT DIGESTION AND ABSORPTION FORMULATION TO AID IN MEASURING FAT ABSORPTION

STATEMENT REGARDING FEDERALLY SPONSORED RESEARCH OR DEVELOPMENT

This invention was made with government support under Contract Nos. R-44-DK-48190 and R-42-DK-448537 between the National Institutes of Health and BioChem Analysis Corporation. The United States Government has certain rights in this invention.

BACKGROUND OF THE INVENTION

1. Field of the Invention

The present invention relates generally to a method and formulation for measuring fat digestion and absorption and more specifically to a method and formulation for measuring fat digestion and absorption in individuals predisposed to inadequate fat digestion and absorption due to disease.

2. Background of the Invention

Certain diseases prevent persons from properly digesting and/or absorbing fat (triglycerides). For example, cystic fibrosis, the most common lethal genetic disorder of Caucasian populations, often results in a patient's inability to digest fat. This is due to the patient's pancreas being unable to supply the enzymes in sufficient amounts for hydrolysis. Another example is Celiac disease in which absorption of digested dietary fat is impaired due to reduced surface area of the small intestine.

Major advances in cystic fibrosis treatment have increased the life expectancy of patients with cystic fibrosis to more than 30 years. As no treatment is currently on the horizon to alleviate the pancreatic/gastrointestinal components of the disease, there is a growing population of cystic fibrosis patients who require life-long nutritional management. The diets of these patients generally are supplemented with pancreatic enzymes. To assure proper enzyme dosage, however, an accurate measurement of a patient's fat digestion and absorption is required.

A number of methods for determining the extent of fat digestion exist. For example, a direct and somewhat unpleasant method involves duodenal intubation and subsequent measurement of enzyme levels withdrawn from the intestine. The procedure is highly invasive, specialized, expensive and difficult to use in young children.

A myriad of indirect measurement procedures based on the appearance of a test substance in bodily fluids such as blood, urine, or breath are also available. These procedures have drawbacks, such as limitations related to the sampling compartment because of the underlying disease, and complications due to disease of related effects on other organ systems, such as the liver and the kidneys, which can lead to inaccurate results.

As an example of the limitations of current fat digestion and absorption measurement techniques, the problems inherent in the $^{13}$C-labeled fat breath test are highlighted below:

1.) Conversion rate of absorbed label to $CO_2$ is influenced by the metabolic status of the individual. (e.g. liver function);
2.) $CO_2$ excretion is effected by lung function;
3.) Variations in body fat content influence the rate of $CO_2$ excretion;
4.) Breath samples are not easily obtained from infants and young children; and
5.) Long (6 to 12 hours) breath sampling times are required.

There are analogous limitations for tests which rely on the appearance of a test substance in blood or urine. Generally, appearance methods are unsuitable for quantitative measurements of gastrointestinal absorption of fat.

A widely used method for measuring fat absorption is the "72-hour stool fat test" (72-h SFT). This test requires that a patient consume 100 grams of fat daily for at least three days, during which the stools are collected for measurement of total fat content. The 72-h SFT is considered the "Gold Standard" for the purpose of determining a patient's ability to digest and/or absorb dietary fat.

However, there are many limitations to the 72-h SFT method. Overall, it is tedious and difficult to perform accurately. For example, a constant fat intake for at least three days is required. Also, quantitative collection of stools, (typically by the patient) is not assured. Only the most diligent adult patients supply accurate information regarding fat intake and accurate stool collection. Hospitalization and close monitoring is required for other adult patients, infants and children, which makes the procedure expensive. As a result, the 72 h SFT is most reliable to detect only significant steatorrhea (excessive fat in stool). Similarly, variability in the coefficient of fat absorption from test to test may be large.

A need exists in the art for an easy and economical method and formulation for directly measuring fat digestion and/or absorption under conditions of normal dietary intake. The method and formulation should depend neither on a patient's skill in collecting all stool for several days, nor in assuring constant fat intake for such a long period of time. The new method should be accurate, reliable, reproducible and noninvasive so as to facilitate easy monitoring and medical management of underlying disease. The results of the new method and formulation would be particularly useful in repetitive monitoring of changes in fat digestion as is recommended for patients with cystic fibrosis.

SUMMARY OF THE INVENTION

It is an object of the present invention to provide a method and formulation for measuring fat digestion and/or absorption which overcomes many of the disadvantages of the prior art.

Another object of the present invention to provide a simple method for accurately measuring fat digestion and/or absorption in patients. A feature of the invention is the patient intake of a single formulation, in the form of a tablet or similar medium, and the subsequent collection of a small amount of stool from a single bowel movement. An advantage of the invention is its administration during normal dietary intake, therefore obviating the need for constant fat intake and obviating the need to collect all stools from a patient. Another advantage of the invention is its ability to detect fat malabsorption of clinical importance before some clinical symptoms occur.

Yet another object of the present invention is a convenient method for collecting stool for subsequent analysis of fat absorption, particularly in cystic fibrosis patients. A feature of the method is the use of stool colorant. An advantage of the method is a one-time collection of stool containing the colorant for subsequent analysis. Another advantage is that the results of the method are highly reproducible.

Still another object of the present invention is to provide a formulation for use in determining fat maldigestion and fat malabsorption. A feature of the formulation is the combination of an isotope-labeled triglyceride, a nonabsorbable fecal marker and a colorant to provide an easy-to-dispense form for self administration. An advantage of using this formulation is the noninvasive and one-step administration and collection method associated with its use to determine levels of fat digestion and absorption in patients.

In brief, a method for measuring fat digestion and/or absorption in a person is provided comprising feeding the person a specific amount of labeled fat, a specific amount of a nonabsorbable marker, and a means for coloring stool (e.g., a visual marker); allowing the fat, the nonabsorbable marker and the stool coloring means to travel through the digestive tract of the person; monitoring stool from the person for the appearance of the coloring means; collecting stool containing the coloring means; and measuring the amount of nonabsorbable marker and labeled fat in a small amount of the colored stool to determine the portion of fat digested and/or absorbed by the person.

Also provided is a formulation which when ingested by a person and later partially retrieved from the digestive system of the person can aid in determining fat digestion and/or absorption characteristics of the person, the formulation comprising a labeled fat; a marker which has the same absorption kinetics as said fat; and a dye mixed with said fat and said marker.

BRIEF DESCRIPTION OF THE DRAWING

The present invention together with the above and other objects and advantages may best be understood from the following detailed description of the embodiment of the invention illustrated in the drawing, wherein.

DETAILED DESCRIPTION OF THE INVENTION

The invented method provides a reliable, highly accurate test for fat digestion and absorption that can be self-administered. The method has broad utility which includes the following:

1.) Aids in evaluating persons for the presence or absence of fat maldigestion and malabsorption, even when no clinical signs of the underlying disorder are present;
2.) Assists in monitoring the course of disorders underlying maldigestion or malabsorption; and.
3.) Helps clinicians optimize therapy for individual patients.

The method is based on two principles. First, that a triglyceride representative of dietary neutral fats in the human diet can be labeled with a non-radioactive isotope (any stable isotope such as $^{13}C$ is suitable) so that its residual presence in stool during several days after its administration quantitatively reflects the residual dietary fat consumed during the same period. Second, that a trace amount of nonabsorbable salt, such as chloride or sulfide salts containing an element or elements from the lanthanide group, can be used as a nonabsorbable marker. When this marker is administered simultaneously, it is completely nonabsorbed by the person and evacuated in feces during the same period of evacuation of the labeled fat.

The inventors have found that certain lanthanide salts (e.g. $DyCl_3$) are quantitatively excreted by patients and follow the same excretion kinetics as labeled triglycerides. Thus, when a known amount of both the marker and labeled fat are consumed with any meal, subsequent chemical analysis of both the labeled fat and lanthanide in any sample of stool containing them permits accurate and rapid measurement of the fat absorbed.

An additional feature of the method is the simultaneous administration of a fecal colorant with the nonabsorbable marker and labeled fat. This obviates the need for collecting all stools subsequent to fat administration. Instead, only a portion of the stool showing the presence of colorant need be collected for subsequent analysis.

Figure 1:
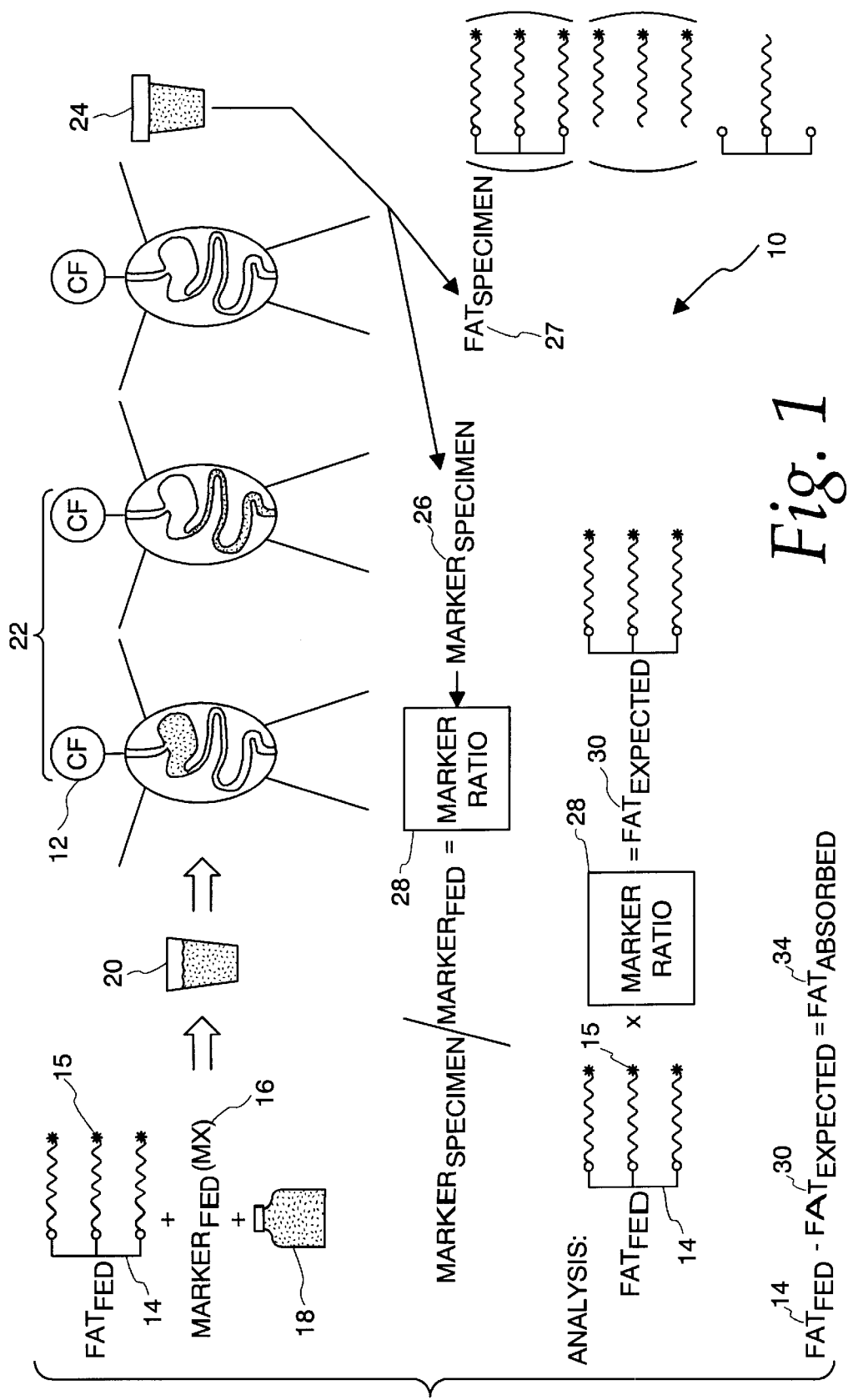
FIG. 1 is a flow diagram of an exemplary process illustrating the present invention.

An exemplary method is depicted generally in FIG. 1 as numeral 10. As an initial step, a specific amount of suitable fat 14, labeled with an isotope 15, is prepared in a specific amount ($FAT_{fed}$).

Prior to feeding to the patient, the fat is mixed with a specific amount ($Marker_{fed}$) of nonabsorbable marker 16 and a stool dye 18 to create a mixture 20. The mixture is administered to the patient 12 and allowed to be metabolized by the patient in the normal course of digestion 22. The patient monitors stool color for appearance of the dye 18 and selects a stool specimen 24 which indicates the presence of the dye.

The specimen is analyzed for the amount of nonabsorbable Marker ($Marker_{specimen}$) 26 and labeled fat ($Fat_{specimen}$) 27. The ratio of $Marker_{specimen}$ to $Marker_{fed}$ is used as a multiplier 28 to determine the amount of fat expected 30 to be excreted if all stools evacuated for several days had been collected and analyzed completely ($Fat_{expected}$). As a last step, the amount of fat so determined ($Fat_{expected}$) is subtracted from ($Fat_{fed}$) to obtain the amount of labeled fat absorbed 34 by the patient 12.

A salient feature of the above stated method is that a single stool sample will yield accurate and reproducible data regarding maldigestion and/or malabsorption of fat by the patient.

The above procedure is easily followed by providing patients with test kits containing all ingredients premixed. Such premixed entities can take the form of a tablet, a liquid, a powder or similar medium. All isotopic and marker analysis of specimens are performed by persons of ordinary analytical skill in typically equipped isotope-handling laboratories.

Fat Dose- and Chemical Forms and Label Position Detail

Dietary fat consists primarily of triglycerides with a majority of these being of mixed fatty acid composition. Fatty acids differ from each other in their chain-length and degree of unsaturation. Fatty acids in the human diet include the following: octanoic acid (8:0), myristic acid (C12:0), palmitic acid (C16:0), stearic acid (C18:0); oleic acid (C18:1), and linoleic acid (C18:2). The last four fatty acids are the most common fatty acids of the various triglycerides present in animal fats and vegetable oil found in human diets.

In the present invention, $^{13}C$-label is incorporated in the fatty acid portion of a selected triglyceride. Inasmuch as a majority of dietary triglycerides are of mixed fatty acid composition, suitable triglycerides also include the mixed variety. Therefore, a myriad of triglycerides, are suitable fat candidates, including but not limited to 1,3-di-stearoyl2 [$^{13}C$] octanoyl glycerol, 1,3-dioleoyl2[$^{13}C$] octanoyl glycerol, triolein, tripalmitin, trioctanoin, and combinations thereof. Three $^{13}C$-labeled triglycerides are commercially available through Cambridge Isotopes Laboratories, Cambridge, Mass.: triolein, tripalmitin, and trioctanoin.

The inventors have found that the chain-length, degree of saturation and position of labels on the fatty acids of selected triglycerides determine the sensitivity and specificity of the invented method and formulation to various disorders of fat maldigestion and fat malabsorption. For example, if $^{13}$C-palmitic acid is incorporated in positions 1 and 3 (sn-1,3) of the triglyceride, the resulting labeled triglyceride is sensitive to both maldigestion (wherein pancreatic enzymes cleave at positions 1 and 3) and malabsorption. Such a triglyceride is ideal to measure generalized steatorrhea due to different mechanisms.

Alternatively, if $^{13}$C is incorporated at position 2 (sn-2) of the triglyceride in the form of $^{13}$C-octanoic acid (8:0), the resulting customized triglyceride is not sensitive to fat malabsorption disorders such as celiac disease inasmuch as hydrolysis of the triglyceride releases the $^{13}$C-label as 2-monoglyceride. 2-monoglyceride with octanoic acid is highly soluble, making it easily absorbable and therefore not affected by celiac disease. However, this triglyceride is sensitive to disorders of the pancreas that cause pancreatic insufficiency (e.g. cystic fibrosis). Furthermore, the chain length and degree of unsaturation of the unlabeled fatty acid incorporated at positions 1 and 3 further affect the degree of pancreatic insufficiency. For example, 1,3-distearin (18:0) is more sensitive to pancreatic insufficiency than 1,3-diolein (18:1).

The minimum dose of $^{13}$C-labeled triglyceride required is estimated based on the following rationale: The $^{13}$C-labeled tripalmitin used by the inventors contains 48.1 mg of excess $^{13}$C per gram, that is, 48.1 mg of $^{13}$C in excess of that due to carbon of natural isotopic composition. If an average absorption of 50 percent is assumed, then total fecal excretion of the excess $^{13}$C should be roughly 24 mg for a 1 gram dose. A stool containing 1 percent of the excreted label would, thus, contain 0.24 mg of $^{13}$C in excess. The routinely achieved measurement precision for $^{13}$C measurements (atom %) in fecal samples is approximately 0.1 percent (RSD). For a daily stool output of 10 grams total carbon (100 mg $^{13}$C), 0.1 percent precision corresponds to 0.1 mg of background $^{13}$C. Administration of 1 gram of $^{13}$C-labeled tripalmitin, under these assumed conditions, would result in a $^{13}$C excess content for stools containing 1 percent of the unabsorbed label of 0.245 mg, which corresponds to about 2 σ (two standard deviations) of the measurement precision. Thus, the dose chosen is 1 g $^{13}$C-labeled tripalmitin for an adult. Assuming an average body weight of 50 kilograms, this corresponds to 20 mg/kg, which corresponds to the dose reported in the literature for breath tests.

Similar estimates are made when using other $^{13}$C-labeled triglycerides, depending on the specifics of the $^{13}$C enrichment.

Marker Dose- and Chemical-Forms Detail

Generally, the invented method and formulation provides a detection level of one percent of the amount of nonabsorbable marker that is fed to a patient. As such, dose levels for the marker are chosen so that one percent of the dose excreted in any stool corresponds to 2 σ of a marker's daily background. Previous research by one of the inventors has determined that the expected background content of lanthanides (such as dysprosium) in feces should be 0–10 μg per day (μg/day), given an average value of 3.4±7.8[2σ] obtained from the analysis of 15 daily collections from four adults. Thus, for an average adult, the dose of lanthanide marker is approximately 1 mg. Generally, lanthanide marker doses of between 20 and 50 μg/kg body weight provide good results.

Exemplary Protocol

The following protocol was carried out on nine cystic fibrosis patients in a medical center. Each patient received a single dose of $^{13}$C-palmltin (0.700 g) mixed with peanut butter and Dy (1.013 mg) added to milk. Both compounds were fed as part of a meal. Individual stools were collected for five days. If analysis is not performed immediately, the specimens can be frozen.

Each stool was transferred to a tared plastic container and weighed accurately. When thawed, the stool is homogenized and a weighed fraction taken for analysis. The fraction was gently heated to approximately 100° C. until dry (12–24 hours). Each dried sample was ground to a fine powder from which weighed subsamples were taken for measurement of $^{13}$C-excess and Dy. All carbon isotopic analyses were performed with an Europa Scientific 20/20 isotope ratio mass spectrometer equipped with Automated Nitrogen Carbon Analyzer (ANCA). All analyses of Dy were carried out with neutron activation analysis. A detailed protocol for Dy analysis is disclosed in Schuette, S.A. et al. Dysprosium as a non-absorbable fecal marker for studies of mineral absorption with stable isotope tracers in human subjects. J Am Coll. Nutr. 12:pp 307–15, 1993, and incorporated herein by reference.

Dy content of each stool was calculated from the results of Dy measurements performed on the stool's subsample, the dry/wet ratio of each stool, and the total wet weight of each stool. The resulting data were expressed as percent of Dy intake present in each stool. From analysis of $^{13}$C (atom percent) and total carbon performed for each subsample, total $^{13}$C-excess excreted in each stool was calculated according to the following equations:

$$R=[13.0033551(\text{atom \% } ^{13}C)]/12.000000(100\text{-atom \% } ^{13}C)] \quad \text{Eq.1}$$

$$^{13}C^*_{stool}=(\{R+RR^0-R^*-R^*R\}/[RR^0-R^*+RR^*])(\text{Total C}) \quad \text{Eq.2}$$

where $^{13}C^*_{stool}=^{13}$C-excess in each stool; and where R, R*, and R⁰ are $^{13}C/^{12}C$ ratios (wt/wt) for fecal sample of interest, labeled tripalmitin, and baseline fecal sample, respectively. Values of R are calculated from the measured atom percent values using Equation 1.

The results obtained by the inventors indicate that lanthanide salts (e.g. DyCl₃) are nonabsorbable markers in human digestive processes. The results also indicate that $^{13}$C-excess in each stool (expressed as the fraction of total recovered in all stools for any patient) is the same as its corresponding Dy (also expressed as a fraction of the total recovered).

Table 1 below discloses the correlation between lanthanide recovered and excess $^{13}$C recovered. Recoveries of Dy were 93.6 percent or greater in eight of the nine patients with a mean (±1σ) of 108 (±9.9) percent. In these patients, excretion of $^{13}$C-label was ≧67.9 percent of the dose. In contrast Dy recovery for CF1 was only 29.5 percent of the dose, probably the result of incomplete collection of stool.

TABLE 1

Recoveries of Dy and $^{13}$C-excess in cystic fibrosis patients.

| Patient Code | Dy Recovered in all stools (% dose) | $^{13}$C-Excess recovered in all stools (% dose) |
|---|---|---|
| CF#1 | 29.5 | 28.8 |
| CF#2 | 106.7 | 72.9 |
| CF#3 | 114.9 | 93.3 |
| CF#4 | 93.6 | 69.3 |
| CF#5 | 101.8 | 67.9 |
| CF#6 | 118.5 | 107.2 |
| CF#7 | 116.3 | 96.2 |

TABLE 1-continued

Recoveries of Dy and $^{13}$C-excess in cystic fibrosis patients.

| Patient Code | Dy Recovered in all stools (% dose) | $^{13}$C-Excess recovered in all stools (% dose) |
|---|---|---|
| CF#8 | 118.9 | 79.6 |
| CF#9 | 94.2 | 80.6 |

Figure 2:
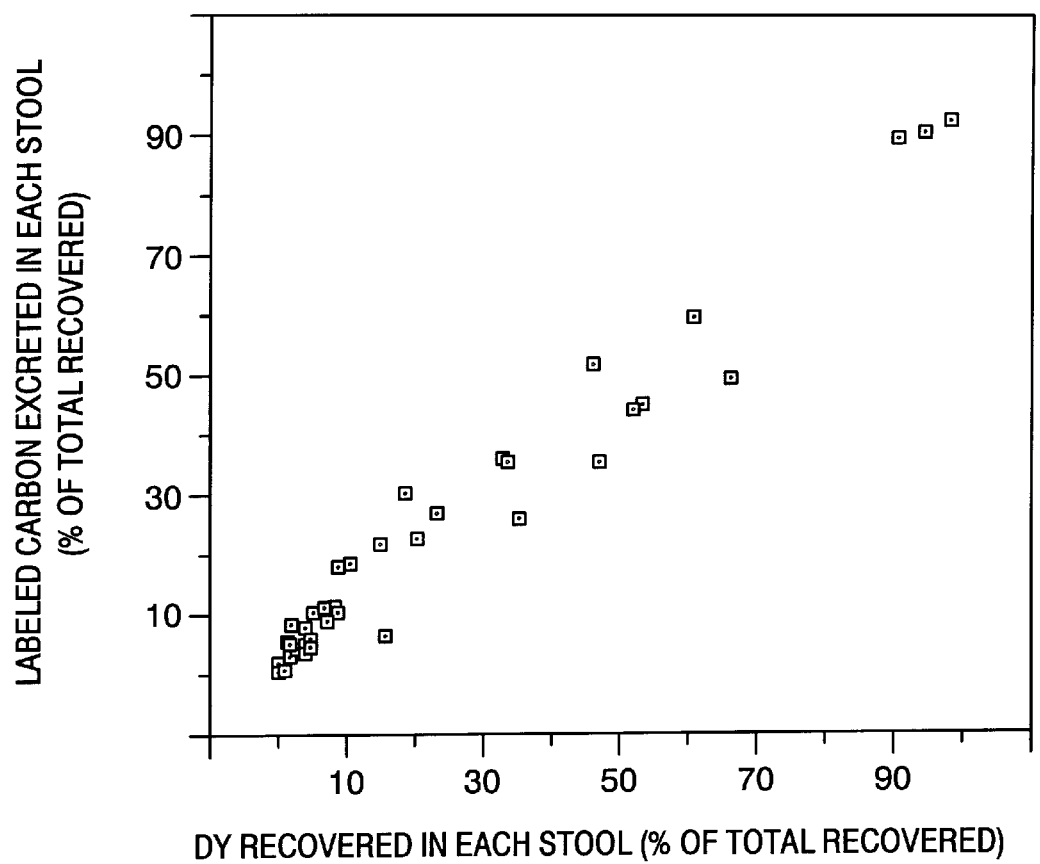
FIG. 2 is a graph comparing the excretion kinetics of lanthanide with $^{13}C$ in the digestive system, in accordance with features of the present invention.

FIG. 2 illustrates the equivalency of the excretion kinetics of Dy and $^{13}$C-labeled triglyceride. The graph depicted in FIG. 2 plots $^{13}$C-excess in each stool against its Dy content, for all stools obtained from the nine patients. The correlation between Dy and isotope kinetics, as depicted in the data discussed supra, allows for an accurate determination of fat assimilation to be made when just one stool is collected, the only caveat being that the stool must contain both Dy and the isotope. To isolate the specifically enriched stool, a stool colorant is thoroughly mixed with the Dy/isotope cocktail prior to ingestion. Subsequent to ingestion, stools are monitored for appearance of the colorant. Upon appearance of the colored stool, the stool is isolated and used for analysis.

Various colorants are available for use in this one-stool retrieval method, including but not limited to, carmine red and brilliant blue. The colorant is added in an approximate 1.0 mg/kg weight ratio of colorant to patient body weight.

While the invention has been described with reference to details of the illustrated embodiment, these details are not intended to limit the scope of the invention as defined in the appended claims.

The embodiment of the invention in which an exclusive property or privilege is claimed is defined as follows:

What is claimed is:

1. A method for measuring fat assimilation in a person comprising:
   a) feeding the person labeled fat, nonabsorbable marker, and a means for coloring stool;
   b) allowing the labeled fat, marker and stool coloring means to travel through the digestive tract of the person;
   c) monitoring stool from the person for the appearance of the coloring means;
   d) collecting stool containing the coloring means; and
   e) measuring the amount of marker and labeled fat in the stool to determine the portion of fat assimilated by the person.

2. The method as recited in claim 1 wherein the step of measuring the amount of marker and labeled fat in the stool further comprises:
   a) comparing the amount of marker measured in one stool to the specific amount of marker fed to the person to determine the ratio of measured marker to fed marker; and
   b) comparing the proportion of measured marker to fed marker with the ratio of measured labeled fat to fed labeled fat to determine the amount of fed labeled fat absorbed by the person.

3. The method as recited in claim 1 wherein the step of collecting stool comprises isolating one stool specimen.

4. The method as recited in claim 1 wherein the labeled fat is selected from the group consisting of 1,3-distearyl, 2[$^{13}$C] octanoyl glycerol, 1,3-dioleyl, 2[$^{13}$C] octanoyl glycerol, triolein, tripalmitin, trioctanoin, and combinations thereof.

5. The method as recited in claim 1 wherein the person is fed the labeled fat, marker and colorant simultaneously.

6. The method as recited in claim 1 wherein the nonabsorbable marker contains a lanthanide element.

7. The method as recited in claim 1 wherein the nonabsorbable marker is a salt of a lanthanide element.

8. The method as recited in claim 1 wherein the coloring means is selected from the group consisting of carmine red and brilliant blue.

9. The method as recited in claim 1 wherein the label is an isotope selected from the group consisting of carbon-13, and deuterium.

10. A formulation which when ingested by a person and later partially retrieved from the digestive system of the person can aid in determining fat assimilation characteristics of the person, comprising:
    a) a labeled fat;
    b) a marker which has the same absorption kinetics as said labeled fat; and
    c) a dye mixed with said labeled fat and said marker.

11. The formulation as recited in claim 10 wherein the labeled fat is present in a fat to person weight ratio of approximately 20 mg/kg.

12. The formulation as recited in claim 10 wherein the marker is present in a marker to person weight ratio of approximately 20 µg/kg.

13. The formulation as recited in claim 10 where said labeled fat is a neutral fat.

14. The formulation as recited in claim 10 wherein said labeled fat is selected from the group consisting of 1,3-distearyl, 2[$^{13}$C] octanoyl glycerol, 1,3-dioloeyl, 2[$^{13}$C] glycerol, triolein, tripalmitin, trioctanoin, and combinations thereof.

15. The formulation as recited in claim 10 wherein said marker is not absorbed by the person.

16. The formulation has recited in claim 10 wherein the marker is a salt of a lanthanide element.

17. The formulation as recited in claim 10 wherein the marker is a chloride salt of a lanthanide element.

18. The formulation as recited in claim 10 wherein the dye is selected from the group consisting of carmine red and brilliant blue.

19. The formulation as recited in claim 10 wherein the dye is present in a weight ratio to the patient of approximately 1.0 mg/kg.

* * * * *

UNITED STATES PATENT AND TRADEMARK OFFICE
CERTIFICATE OF CORRECTION

PATENT NO. : 6,006,754
DATED : December 28, 1999
INVENTOR(S) : Janghorbani, et al.

It is certified that error appears in the above-indentified patent and that said Letters Patent is hereby corrected as shown below:

Title page, Item [73], please insert --Children's Hospital Research Foundation, Chicago, Ill.-- as the second Assignee.

Signed and Sealed this

Twenty-sixth Day of December, 2000

Attest:

Q. TODD DICKINSON

*Attesting Officer*          *Director of Patents and Trademarks*

UNITED STATES PATENT AND TRADEMARK OFFICE
CERTIFICATE OF CORRECTION

PATENT NO. : 6,006, 754
DATED : December 28, 1999
INVENTOR(S) : Janghorbani et al It is certified that error appears in the above-indentified patent and that said Letters Patent is hereby corrected as shown below:

Item [73], please insert --Children's Hospital Medical Center, Cincinnati, OH-- as the second Assignee.

UNITED STATES PATENT AND TRADEMARK OFFICE
CERTIFICATE OF CORRECTION

PATENT NO. : 6,006,754
DATED : December 28, 1999
INVENTOR(S) : Jaghorbani et al.

It is certified that error appears in the above-indentified patent and that said Letters Patent is hereby corrected as shown below:

Claim 7, column 8, line 14, after "a", first occurrence, insert --chloride--.

Claim 16, column 8, line 44, after the word "formulation" delete "has" and insert the word --has--.

Signed and Sealed this

Twenty-fourth Day of April, 2001

Attest:

NICHOLAS P. GODICI

Attesting Officer

Acting Director of the United States Patent and Trademark Office